United States Patent [19]

Mylroie

[11] Patent Number: 5,861,535
[45] Date of Patent: Jan. 19, 1999

[54] REDUCTIVE ALKYLATION PROCESS TO PREPARE TERTIARY AMINOARYL COMPOUNDS

[75] Inventor: Victor L. Mylroie, Fairport, N.Y.

[73] Assignee: Eastman Kodak Company, Rochester, N.Y.

[21] Appl. No.: 935,684

[22] Filed: Sep. 23, 1997

[51] Int. Cl.⁶ .................. C07C 209/26; C07C 209/24
[52] U.S. Cl. .................. 564/397; 544/402; 544/403; 546/143; 564/395; 564/396; 564/398; 564/218; 564/95; 564/415
[58] Field of Search .................. 564/395, 396, 564/397, 398, 278, 95, 415; 546/143; 544/402, 403

[56] References Cited

U.S. PATENT DOCUMENTS

| | | | |
|---|---|---|---|
| 3,963,780 | 6/1976 | Manning | 260/570.8 R |
| 4,229,374 | 10/1980 | Slaugh et al. | 260/563 R |
| 4,760,183 | 7/1988 | Papenfuhs et al. | 564/398 |
| 4,967,004 | 10/1990 | Maki et al. | 564/397 |
| 5,276,193 | 1/1994 | Maki et al. | 564/397 |

FOREIGN PATENT DOCUMENTS

| | | |
|---|---|---|
| 0 602 552 A1 | 12/1992 | European Pat. Off. . |
| 56339 | 8/1991 | Hungary . |
| 62-164653 | 7/1987 | Japan . |
| 62-258345 | 11/1987 | Japan . |
| 62-258346 | 11/1987 | Japan . |
| 3-232846 | 10/1991 | Japan . |
| 6-009513 | 1/1994 | Japan . |
| 8-143523 | 6/1996 | Japan . |
| 450444 | 8/1977 | Spain . |

OTHER PUBLICATIONS

N–Benzyl–N–Ethylaniline; An Alternative Synthetic Approach, Ayyangar et al, J. Chem. Tech. Biotechnol, 1990, 51, 293–300.
Research Disclosure 37651, Aug. 1995, p. 564.
Catalysis of Organic Reactions, Pascoe, M.Dekker, Inc. 1992.
Catalysis of Organic Reactions, Kosak et al, Dekker, Inc. 1994.
Catalysis of Organic Reactions, Kosak, Dekker, Inc. 1984.

*Primary Examiner*—Shailendra Kumar
*Attorney, Agent, or Firm*—J. Lanny Tucker

[57] ABSTRACT

Tertiary aminoaryl compounds, such as N,N'dialkylaminoaryl compounds, are prepared using successive reductive steps without isolation therebetween, at high temperature and pressure. A nitroaryl compound is reduced using a ketone as both solvent and reactant in a reductive environment, and the resulting intermediate is further reacted with an aldehyde in the same reaction mixture without isolation to provide the second substituent on the amino group.

20 Claims, No Drawings

REDUCTIVE ALKYLATION PROCESS TO PREPARE TERTIARY AMINOARYL COMPOUNDS

FIELD OF THE INVENTION

This invention relates to a method of chemical synthesis. In particular, it relates to a method of preparing tertiaryaminoaryl compounds such as N,N'-diakylaminoaryl compounds, by successive reductions of nitroaryl compounds. These materials have utility in the preparation of cyan dyes that are useful in thermal dye transfer materials.

BACKGROUND OF THE INVENTION

There are a number of commercial processes for preparing N,N'-dialkylphenyl compounds using several synthesis steps. For example, U.S. Pat. No. 4,760,183 (Papenfuhs et al) describes a process of reducing aromatic nitro compounds to the corresponding amines, followed by reaction with an alkylating agent to replace the hydrogens on the amines with alkyl groups. A number of problems, including low yields and unwanted side reactions, are described for this process. The Papenfuhs et al patent then describes an alleged improvement using aldehydes as reductive agents in various solvents including alcohols. Catalytically activated hydrogen and precious metal catalysts are also used in the basic reaction environment.

*Research Disclosure* publication 37651 (August, 1995) describes the preparation of N-{4-[(methylethyl)amino]phenyl}acetamide by reacting N-(4-nitrophenyl)acetamide in the presence of 5% platinum on carbon catalyst, acetone and ethanol. This step reduces the nitro group on the starting material to an amine. Alkylation during two steps adds two alkyl groups, with isolation between the two steps. The second step is carried out in the presence of diethylsulfate which is considered a carcinogenic material and is therefore difficult to handle. Besides the multiple steps and difficult reactants, this process provides low yields of 60–65%.

It would be desirable to have an improved process that requires less steps and hazardous materials, and provides improved yields.

SUMMARY OF THE INVENTION

The problems of prior processes noted above are solved with a method for preparing a tertiary aminoaryl compound comprising reacting a secondary aminoaryl at high temperature and pressure with an aldehyde in a reductive environment and in the presence of a ketone and a hydrogenation catalyst for at least 2 hours.

This invention also provides a method for preparing a tertiary aminoaryl compound, comprising:

A) reducing a nitroaryl in the presence of a ketone solvent in a reductive environment to provide a secondary aminoaryl compound, and B) without isolation from the reaction mixture used in step A, and upon the addition of an aldehyde, reacting the secondary aminoaryl compound with the aldehyde in the presence of the ketone and in a reductive environment at high temperature and pressure for at least 2 hours to provide the tertiary aminoaryl compound.

The process of this invention avoids isolation between successive reduction steps required in previous alkylation processes, and avoids the use of undesirable carcinogenic alkylating agents. Thus, the process is safer and more efficient. In most instances, yields were increased by at least 25–30% over previous processes.

Thus, a tertiary aminoaryl compound can be prepared by reducing an aromatic nitro compound in the presence of a ketone that acts both as a solvent and a reactant, and a noble metal catalyst Reduction of the nitro compound takes place very rapidly, and the reduced compound subsequently reacts with the ketone to form a Schiff type base which is further reduced to a mono-substituted aminoaryl intermediate (thus, a secondary aminoaryl compound). Without isolation of this intermediate, an aldehyde is added to the reaction mixture and further reduction takes place in the presence of the ketone to provide the desired tertiary aminoaryl compound at yields of 99.2–99.5%.

DETAILED DESCRIPTION OF THE INVENTION

A variety of compounds can be made using the process of this invention. The process can be used to incorporate one or more disubstituted (tertiary) amino groups onto the ring of an aryl group, such as phenyl, naphthyl, anthryl, methylphenyl, phenylacetamide or other substituted aryl group that would be readily apparent to one skilled in the art, This aryl group is also substituted with a nitro group. By "aryl group" or "aryl compound" is also meant a carbocyclic aryl group (such as phenyl or naphthyl) that has a heterocyclic ring fused thereto. The fused portion can have from 3 to 5 carbon, nitrogen, sulfur or oxygen atoms in a chain that is attached to adjacent carbon atoms of the carbocyclic aryl portion of the molecule. One such compound is isoquinoline.

Thus, the nitro-substituted aryl compound can also be substituted with one or more alkyl groups (having 1 to 10 carbon atoms) or aryl groups (carbocyclic or heterocyclic groups) having up to 10 atoms in the ring.

Preferably, the nitro-substituted aryl starting material is also substituted with an N-blocking group in position para to the nitro group. Such blocking groups are generally electron withdrawing groups, and include, but are not limited to, such groups as —NHCOR$_1$, —NHSO$_2$R$_1$, alkoxy (having up to 10 carbon atoms), or an N-heterocyclic group having 5 to 10 atoms in the ring (such as piperazinyl, triazolyl and p-isoxazinyl), that serve to provide protected radicals that can be used in later reactions. Preferably, the blocking group is —NHCOR$_1$ or —NHSO$_2$R$_1$.

R$_1$ is an alkyl group of 1 to 10 carbon atoms (branched or linear, including methyl, ethyl, isopropyl, t-butyl and hexyl), which alkyl can be substituted with one or more oxyalkyl, aryl or halo groups. R$_1$ can also be a substituted or unsubstituted phenyl group (for example, substituted with one or more halo, lower alkyl of 1 to 3 carbon atoms, or nitro groups), an amino group (primary or secondary substituted with an alkyl or phenyl group), or a trihalo group (such as —CCl$_3$ or —CF$_3$). More preferably, the blocking groups are —NHCOR$_1$ wherein R$_1$ is alkyl of 1 to 3 carbon atoms. An N-acetyl blocking group is most preferred.

The tertiary aminoaryl compounds prepared using the present invention can generally be represented by structure I:

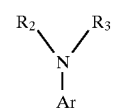

wherein Ar is an aryl group as defined above, and R$_2$ and R$_3$ are independently a substituted or unsubstituted alkyl group having 1 to 10 carbon atoms (branched or linear, substituted or unsubstituted), a substituted or unsubstituted cycloalkyl group having 5 to 10 carbon atoms in the ring (such as cyclohexyl), or a saturated (non-aromatic) heterocyclic ring having 5 to 10 atoms in the ring (composed of carbon and one or more nitrogen, sulfur or oxygen atoms). Preferably, at least one of $R_2$ and $R_3$ is an alkyl group having 1 to 6 carbon atoms. More preferably, both are alkyl groups of the same or different size. Most preferably, each of $R_2$ and $R_3$ is an unsubstituted alkyl of 1 to 4 carbon atoms. The alkyl groups can be substituted, for example, with a phenyl group that can also be substituted with non-electron withdrawing groups.

The compounds of structure I are generally prepared by reducing the corresponding nitro-substituted aryl compound in the presence of a suitable ketone in a reductive environment (described below). This reduction step provides a secondary aminoaryl compound of structure II:

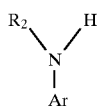

wherein Ar and $R_2$ are as defined above. The $R_2$ group comes from the ketone in the reaction mixture. The intermediate of structure II then is further reduced, without isolation, in the presence of the same ketone and an aldehyde newly introduced to the reaction mixture. The aldehyde provides the $R_3$ group on the final product.

A simplified reaction sequence for the present invention is as follows:

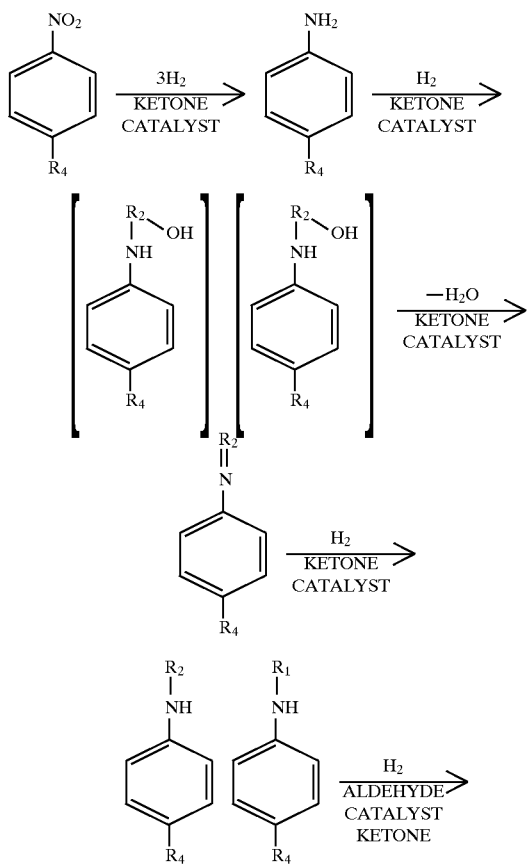

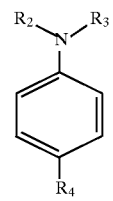

wherein $R_4$ is hydrogen, an alkyl group, an aryl group, the N-blocking group defined above or another suitable substituent, and $R_2$ and $R_3$ are as defined above. Preferably, $R_4$ is an N-blocking group as defined above.

The general reaction procedure can be described as follows:

To a stirred autoclave capable of 1500–2000 psig (105–140 kg/cm$^2$) and heating and cooling capacity, is added a nitro-substituted aryl compound and a suitable non-aromatic ketone (such as acetone, 2-butanone, 2-pentanone, 3-pentanone, 2-hexanone, cyclohexanone, acetophenone, and others that would be readily apparent to a skilled artisan) that serves as both the reaction solvent and reactant to provide a substituent on the amino group, and a suitable noble metal catalyst (such as palladium or platinum or other conventional material) on a carbon support. Preferably, the ketone is acetone. The autoclave is purged with nitrogen and then charged with hydrogen to a pressure of from about 60 to about 1500 psig (0.07–105 kg/cm$^2$), and heating and agitation (stirring) are begun. The rapidly occurring reaction is exothermic and requires cooling. After the initial reaction has begun, the temperature of the reaction mixture is adjusted to from about 90° to about 150° C., and the mixture is stirred for from about 2 to about 24 hours. Preferred reaction conditions include a pressure of from about 750 to about 1200 psig (53–85 kg/cm$^2$) and a temperature of from about 90° to about 120° C. Optimum conditions for many reactants are about 1000 psig (70 kg/cm$^2$) and about 110° C.

At the conclusion of this step, without isolating the intermediate reaction product, a suitable aldehyde is added to the reaction mixture. Suitable aldehydes are compounds having a single aldehyde moiety and that provide a second substituent on the amino group, and include any straight or branched chain acyclic aldehyde. Such compounds can be substituted with an aryl group if desired, but such substituents are not preferred. Useful aldehydes include, but are not limited to, acetaldehyde, propionaldehyde, butyraldehyde, valeraldehyde, lauraldehyde, benzaldehyde, p-methoxybenzaldehyde, and others readily apparent to one skilled in the art. The non-aromatic aldehydes are preferred, and acetaldehyde is most preferred.

The aldehyde can be added to the reaction mixture in any suitable manner, with or without the ketone as a solvent. In one embodiment, the reaction mixture is cooled to 35° C., and vented of excess hydrogen. The autoclave is opened, and the aldehyde is added. The autoclave is again purged and charged with hydrogen to a pressure of from about 60 psig to about 1500 psig (0.07–105 kg/cm$^2$), and reaction was carried out at from about 90° to about 150° C. for from about 2 to about 24 hours. Preferred reaction conditions include a pressure of from about 750 to about 1200 psig (53–85 kg/cm$^2$), and optimum conditions are those stated for the first reaction step.

In another embodiment, the reaction pressure and temperature are maintained, and the aldehyde is pumped into the reaction mixture, followed by reaction for at least 2 hours.

After the second reaction time, the reaction mixture is cooled to 35° C., and the catalyst can be removed by filtration.

The desired product can be removed from the reaction mixture using any suitable procedure and used as is, or further reacted. For example, if the desired product has an N-blocking group on the aryl ring, such a group can be removed so the resulting tertiary aminoaryl compound can be further reacted, for example to make a hydrochloride salt. This salt can be then used to prepare various thermal transfer dyes by reaction at the hydrochloride salt moiety.

By way of illustration, and not limitation, Compound A (shown below) can be reacted (after removal of the blocking group) with HCl to form the corresponding hydrochloride salt:

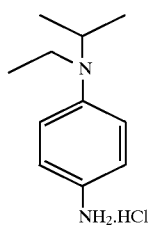

which can then be reacted with

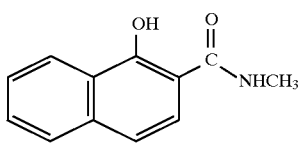

in ammonium hydroxide and isopropyl alcohol to form a thermal transfer dye:

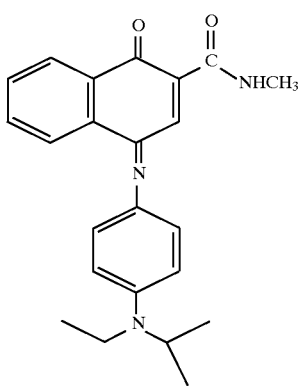

that can be used in the imaging materials and methods described, for example, in U.S. Pat. No. 5,340,789 (Evans et al).

The following representative compounds can be prepared using the appropriate starting materials and the method of this invention:

A

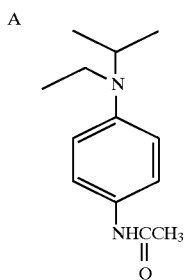

B

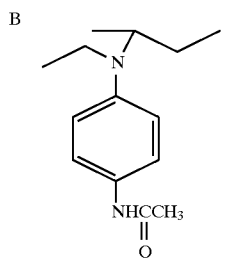

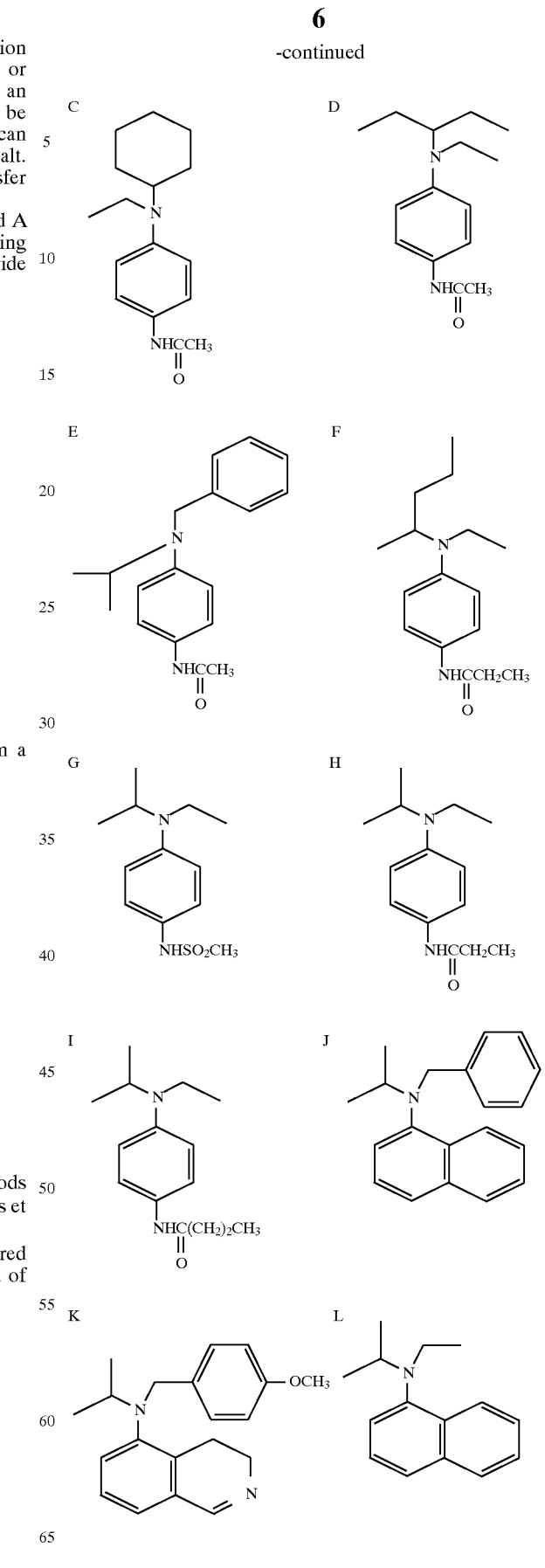

EXAMPLE 2

Preparation of Compound B

Compound B was prepared using the procedure and conditions described in Example 1 except that 2-butanone was used as solvent and reactant in place of acetone. The yield of desired product was 98%.

EXAMPLE 3

Preparation of Compound C

Compound C was prepared using the procedure and conditions described in Example 1 except that cyclohexanone was used as solvent and reactant in place of acetone. The yield of desired product was 95.5%.

EXAMPLE 4

Preparation of Compound D

Compound D was prepared using the procedure and conditions described in Example 1 except that 3-pentanone was used in place of acetone. The yield of desired product was 99.3%.

EXAMPLE 5

Preparation of Compound E

Compound E was prepared using the procedure and conditions described in Example 1 except that benzaldehyde was used in place of acetaldehyde. The yield of desired product was below 90%.

EXAMPLE 6

Preparation of Compound F

Compound F was prepared using the procedure and conditions described in Example 1 except that 2-pentanone was used in place of acetone. The yield of desired product was 98.7%.

EXAMPLE 7

Preparation of Compound G

Compound G was prepared using the procedure and conditions described in Example 1 except that the starting material was p-nitrophenylsulfanilide. The yield of desired product was 95.5%.

EXAMPLE 8

Preparation of Compound H

Compound H was prepared using the procedure and conditions described in Example 1 except that the starting material was p-nitrophenylpropanamide. The yield of desired product was 99.5%.

EXAMPLE 9

Preparation of Compound I

Compound I was prepared using the procedure and conditions described in Example 1 except that the starting material was p-nitrophenylbutanamide. The yield of desired product was 99.5%.

EXAMPLE 10

Preparation of Compound L

Compound L was prepared using the procedure and conditions described in Example 1 except that the starting material was 1-nitronaphthyl. The yield of desired product was 69.4%.

The following examples are intended to illustrate the practice of this invention, and not to be interpreted as limiting in any way. Not every preparation in the examples has been optimized for product yield.

EXAMPLE 1

Preparation of Compound A

Compound A, N-(4-ethyl(1-methylethyl)phenylacetamide, was prepared as follows:

To a 500 ml stirred autoclave equipped with a heating mantle and heating and cooling coils, and capable of operating at pressures of from 0 to 1500 psig (105 kg/cm$^2$) after purging with nitrogen, were added 55 g of p-nitroacetanilide (0.3053 mol), 1.2 g of 3% platinum on carbon support sulfided 50–60% water wet, and 200 ml of acetone. The reaction mixture was purged with nitrogen, charged with hydrogen to 1000 psig (70 kg/cm$^2$), and heated to 100° C. Stirring was continued for about 2 hours with hydrogen being added to maintain the noted pressure.

The reaction mixture was cooled to 35° C., purged with nitrogen, and a sample was checked for completion using thin layer chromatography and a gas chromatography analysis. When the reaction was considered complete, without isolation of the intermediate reaction produce, 2 equivalents (29 g) of acetaldehyde (in 50 ml acetone) were added and the reaction vessel was again purged with nitrogen, charged with hydrogen to 800 psig (56 kg/cm$^2$), and heated to 100° C.

The pressure was adjusted to 1000 psig (70 kg/cm$^2$) after the reaction mixture reached the desired temperature, and stirring was continued for three hours, or until hydrogen consumption stopped. The reaction mixture was then cooled to 35° C., and vented of excess hydrogen. The autoclave was purged with nitrogen and the contents filtered through a supercell pad to remove the catalyst.

Gas chromatography confirmed the desired product in the reaction mixture at a yield of 99.2–99.5%.

EXAMPLE 11

Preparation of Compound M

Compound M was prepared using the procedure and conditions described in Example 1 except that the starting material was 1-nitroisoquinoline, and benzaldehyde was used in place of acetaldehyde. The yield of desired product was 42%.

EXAMPLE 12

Preparation of Compound N

Compound N was prepared using the procedure and conditions described in Example 1 except that the starting material was 4-piperazinylnitrophenyl (also known as nitrophenazine). The yield of desired product was 94.2%.

EXAMPLE 13

Preparation of Compound O

Compound O was prepared using the procedure and conditions described in Example 1 except that the starting material was 4-nitroanisole, and acetophenone was used in place of acetone. The yield of desired product was 88.8%.

EXAMPLE 14

Preparation of Compound P

Compound P was prepared using the procedure and conditions described in Example 1 except that acetophenone was used in place of acetone. The yield of desired product was 84.2%.

The invention has been described in detail with particular reference to preferred embodiments thereof, but it will be understood that variations and modifications can be effected within the spirit and scope of the invention.

I claim:

1. A method for preparing a tertiary aminoaryl compound comprising reacting a secondary aminoaryl at high temperature and pressure with an aldehyde in a reductive environment and in the presence of a ketone and a hydrogenation catalyst for at least 2 hours.

2. The method of claim 1 wherein said reaction is carried out at from about 90° to about 150° C. and from about 60 to about 1500 psig, for from about 2 to about 24 hours.

3. The method of claim 1 wherein said ketone is a non-aromatic ketone.

4. The method of claim 3 wherein said ketone is acetone, 2-butanone, 2-pentanone, 3-pentanone, cyclohexanone, acetophenone or 2-hexanone.

5. The method of claim 4 wherein said ketone is acetone.

6. The method of claim 1 wherein said aldehyde is a straight or branched chain acyclic aldehyde.

7. The method of claim 6 wherein said aldehyde is acetaldehyde, propionaldehyde, butyraldehyde, valeraldehyde, lauraldehyde, benzaldehyde or p-methoxybenzaldehyde.

8. The method of claim 7 wherein said aldehyde is acetaldehyde.

9. The method of claim 1 wherein the tertiary aminoaryl compound has the structure I:

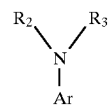

wherein Ar is an aryl group, and $R_2$ and $R_3$ are independently substituted or unsubstituted alkyl group having 1 to 10 carbon atoms, a substituted or unsubstituted cycloalkyl group having 5 to 10 carbon atoms in the ring, or a saturated heterocyclic ring having 5 to 10 atoms in the ring.

10. The method of claim 9 wherein at least one of $R_2$ and $R_3$ is an alkyl group having 1 to 6 carbon atoms.

11. The method of claim 10 wherein both of $R_2$ and $R_3$ are alkyl groups of the same or different size.

12. A method for preparing a tertiary aminoaryl compound comprising:

A) reducing a nitroaryl in the presence of a ketone solvent in a reductive environment to provide a secondary aminoaryl compound, and B) without isolation from the reaction mixture used in step A, and upon the addition of an aldehyde, reacting said secondary aminoaryl compound with said aldehyde in the presence of said ketone and in a reductive environment at high temperature and pressure for at least 2 hours to provide said tertiary aminoaryl compound.

13. The method of claim 12 wherein steps A and B are independently carried out at from about 90° to about 150° C. and from about 60 to about 1500 psig for from about 2 to about 24 hours.

14. The method of claim 12 wherein said ketone is a non-aromatic ketone, and said aldehyde is a straight or branched chain acyclic aldehyde.

15. The method of claim 14 wherein said ketone is acetone, 2-butanone, 2-pentanone, 3-pentanone, cyclohexanone, acetophenone or 2-hexanone, and said aldehyde is acetaldehyde, propionaldehyde, butyraldehyde, valeraldehyde, lauraldehyde, benzaldehyde or p-methoxybenzaldehyde.

16. The method of claim 15 wherein said ketone is acetone and said aldehyde is acetaldehyde.

17. The method of claim 12 wherein said tertiary aminoaryl is represented by the structure I, and said secondary aminoaryl is represented by the structure II:

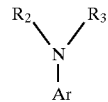

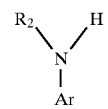

wherein Ar is an aryl group, and $R_2$ and $R_3$ are independently substituted or unsubstituted alkyl group having 1 to 10 carbon atoms, a substituted or unsubstituted cycloalkyl group having 5 to 10 carbon atoms in the ring, or a saturated heterocyclic ring having 5 to 10 atoms in the ring.

18. The method of claim 12 wherein said tertiary aminoaryl compound has the formula:

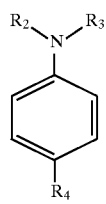

wherein $R_4$ is hydrogen, an alkyl group, an aryl group or an N-blocking group, $R_2$ and $R_3$ are independently an alkyl group of 1 to 6 carbon atoms, or a cycloalkyl group of 6 to 10 carbon atoms wherein at least one of $R_2$ and $R_3$ is an alkyl group.

19. The method of claim 19 wherein $R_4$ is an N-blocking group, and both of $R_2$ and $R_3$ is alkyl group.

20. The method of claim 18 wherein said N-blocking group is —$NHCOR_1$, —$NHSO_2R_1$, alkoxy or an N-heterocyclic group having 5 to 10 atoms in the ring, wherein $R_1$ is an alkyl group of 1 to 10 carbon atoms, phenyl group, amino group or trihalo group.

* * * * *